United States Patent [19]

Streuff et al.

[11] Patent Number: 4,675,182

[45] Date of Patent: Jun. 23, 1987

[54] COMPLEXES OF PROSTAGLANDINS

[75] Inventors: Bernhard Streuff, Cologne; Detlef Mathes, Wuppertal; Bernd Schade, Cologne; Ulrich Schorsch, Duesseldorf, all of Fed. Rep. of Germany

[73] Assignee: Bayer Aktiengesellschaft, Leverkusen, Fed. Rep. of Germany

[21] Appl. No.: 574,789

[22] Filed: Jan. 27, 1984

[30] Foreign Application Priority Data

Feb. 12, 1983 [DE] Fed. Rep. of Germany ....... 3304867
Feb. 12, 1983 [DE] Fed. Rep. of Germany ....... 3304880
Feb. 12, 1983 [DE] Fed. Rep. of Germany ....... 3304864

[51] Int. Cl.[4] .......................................... A61K 31/557
[52] U.S. Cl. ...................................... 424/80; 424/78; 526/264; 514/690
[58] Field of Search .................... 424/78, 80; 526/264; 514/690

[56] References Cited

U.S. PATENT DOCUMENTS

| | | | |
|---|---|---|---|
| 4,036,954 | 7/1977 | Murakoni | 424/176 |
| 4,058,623 | 11/1977 | Hoffmann | 424/317 |
| 4,228,152 | 10/1980 | Ferruti | 424/81 |
| 4,301,146 | 11/1981 | Sandvordeker | 424/80 |
| 4,352,790 | 10/1982 | Johansson | 424/78 |

Primary Examiner—Robert Gerstl
Attorney, Agent, or Firm—Sprung Horn Kramer & Woods

[57] ABSTRACT

The present invention relates to complexes of prostaglandins and crosspovidone, pre-pasted starch or dextrans, a process for the preparation of these complexes, their use in or as medicaments, and medicaments or pharmaceutical formulations containing complexes of prostaglandins or crosspovidone, pre-pasted starch or dextrans.

10 Claims, No Drawings

COMPLEXES OF PROSTAGLANDINS

The present invention relates to complexes of prostaglandins and crosspovidone, pre-pasted starch or dextrans, a process for the preparation of these complexes, their use in or as medicaments, and medicaments or pharmaceutical formulations containing complexes of prostaglandins on crosspovidone, pre-pasted starch or dextrans.

Prostaglandins are naturally occurring substances which are formed via the arachidonic acid metabolism route and have very intensive and specific actions. Examples of known naturally occurring prostaglandins are prostaglandins of the following type:

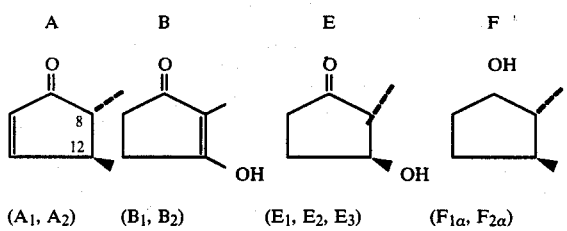

(A₁, A₂)  (B₁, B₂)  (E₁, E₂, E₃)  (F₁ₐ, F₂ₐ)

The individual naturally occurring compounds used their synthetic analogues differ by different substitutions in the two side chains on C-8 and C-12 of the particular five-membered ring, for example by OH groups, double bonds, aliphatic substituents, carboxylic acid radicals and esters thereof.

Prostaglandins are achieved increasing interest because of their intensive and specific biological and pharmacological activities. Those of the E type, called PGE below, are very good for the treatment of hypertension, bronchial asthma, gastrointestinal ulcers and thromboses, and for inducing labour and abortions in mammals, that is to say humans and animals.

However, it is known that prostaglandins, in particular prostaglandin E derivatives, are relatively unstable. This instability has hitherto proved a hindrance to broad pharmaceutical use of the PGE compounds. Decomposition of the E derivatives leads to the corresponding PGA or PGB derivatives in a pH-dependent reaction, with elimination of water:

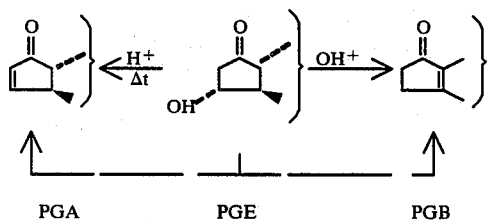

PGA            PGE            PGB

There has therefore been no lack of attempts to stabilise these unstable prostaglandin derivatives.

It is known from Eur. J. Phamacol. 4, 1968, pages 416–420 that solutions of prostaglandins in methanol are stable for up to 40 days, depending on the pH value, at room temperature in the case of PGE₁ and PGE₂. However, medical use is excluded merely because of the toxicity of methanol.

According to a report in Lipids 8, 10, 1973, pages 592–594, PGE₂ loses 5–12% of its activity within one month when stored in ethanol at a temperature of 4° C., and decomposes so rapidly in sodium chloride solution that only 58–62% of its original activity is present after 15 days.

Surprisingly, it has now been found that the stability of prostaglandins can be substantially improved by adsorption onto crosspovidone, pre-pasted starch or dextrans so that, for example, widespread use as medicaments is possible.

In the context of the present invention, furthermore, the term prostaglandins means not only the naturally occurring prostaglandins but also, in particular, derivatives and analogues thereof. By derivatives and analogues there are preferably understood those which differ from the naturally occurring prostaglandins structurally by the type, number and position of functional groups and substituents, and in their activity, especially in respect of selectivity, specificity and potency for individual medical indications and places of action.

The present invention thus relates to complexes of prostaglandins on crosspovidone, pre-pasted starch or dextrans.

The present invention furthermore relates to a process for the preparation of stable prostaglandin formulations in which the prostaglandin is applied in dissolved form to crosspovodine, pre-pasted starch or dextrans and is then dried.

The present invention moreover relates to medicaments containing prostaglandins adsorbed onto crosspovidone, pre-pasted starch or dextrans and to the use of prostaglandins, or derivatives thereof, adsorbed onto crosspovidone, pre-pasted starch or dextrans in or as medicaments and for combating diseases, in particular for combating gastrointestinal ulcers, hypertension, bronchial asthma and thromboses, and for inducing labour and/or abortions in mammals.

In the context of the present invention, crosspovidones are understood as meaning polyvinylpyrrolidone crosslinked by further polymerisation, especially a water-insoluble polyvinylpyrrolidone of this type. In the context of the present invention, crosspovidones which meet the specification of NF XV (National Formulary, 15 Edition, Official Nov. 1, 1981, the U.S. Pharmacoperial Convention, Inc.) are preferred.

In the context of the present invention, pre-pasted starch is understood as meaning naturally occurring starch of any origin which has been made into a paste by a physical or chemical process and has then been dried. Pre-pasted starch is preferably understood as meaning a pre-pasted starch which meets the specification of NF XV. NF XV is published as "The National Formulary", fifteenth edition, Official from July 1st 1980, U.S. Pharmacopcial Convention, Inc.

In the context of the present invention, dextrans is understood as meaning chain-like, branched polysaccharides built up from glucose residues in the 1,4- and 1,6-linkage. Dextrans is preferably understood as meaning those polysaccharides which essentially consist of anhydro-D-glucopyranose units characterised by 1,6-glucosidic bonds and which give D-glucose on complete hydrolysis; these polysaccharides preferably have a molecular weight of between about 1,000 and about 20,000,000, particularly preferably between about 10,000 and about 1,000,000.

Preferred in the present inventions are complexes of prostaglandines on crosspovidone, its production and use.

In the context of the present invention, prostaglandins of the E type, especially prostaglandins substituted on the C 16-atom, are understood as being particularly preferred.

16-Methyl-1-11α,16RS-Trihydroxyprost-13E-en-9one of the following formula I

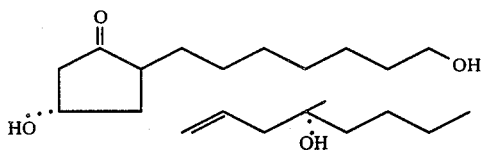

is understood as a very particularly preferred prostaglandin in the context of the present invention.

Since the prostaglandins are substances having an extremely powerful pharmaceutical action and the dosages can be below the milligram range, the process according to the invention is particularly suitable for adsorbing the active compounds onto large amounts of carrier in a simple manner. At very low dosages, a large amount of carrier is even desirable for uniform distribution of the active compound per dose unit (content uniformity).

The weight ratio of prostaglandins, preferably prostaglandin E derivatives, to crosspovidone, pre-pasted starch or dextran in the finished obtained after drying, of prostaglandins on crosspovidone, pre-pasted starch or dextrans should be between 1:1 and 1:10,000, preferably between 1:10 and 1:1,000 and very particularly preferably between 1:100 and 1:500.

Stable prostaglandin formulations in which the above-mentioned weight ratios are also preferred are obtained in the process according to the invention. In the process according to the invention, the appropriate prostaglandin is intimately mixed with, and bonded by, the crosspovidone, pre-pasted starch or dextrans.

Ths can be effected for example, by dissolving the prostaglandin, preferably a prostaglandin E derivative, in an organic or aqueous solvent and also suspending the crosspovidone, pre-pasted starch or dextrans in this solution according to the above-mentioned weight ratios.

The complex is obtained from this suspension by careful drying. Drying according to the invention can be carried out by, for example, freeze-drying, vacuum drying, vacuum drum drying, fluidised bed drying or spray-drying. However, this list is not conclusive, but other careful drying processes can also be used.

Another process variant comprises applying the dissolved prostaglandins directly onto the crosspovidone, pre-pasted starch or dextrans. This can be effected for example, by spraying the solution of active compound onto the carrier material by immersion, a trickling method or fluidised bed application. Drying can again be effected by one of the above-mentioned methods.

The process and subsequent drying are carried out in a manner such that the resulting adsorbates have a certain residual water content. According to the invention and complexes prepared by the process according to the invention should have a residual water content, based on the total weight, of between 0.1 and 15% by weight, preferably between 0.5 and 10% by weight and very particularly preferably between 1 and 5% by weight. According to the invention, it is undesirable to achieve a residual water content of less than 0.1% by weight. The residual water contents are based on finished adsorbates, which are analysed by the determination method of Karl Fischer (Europäisches Arzneibuch (European Pharmacopoeia), volume I, 1974, page 107).

According to the invention, after being dried, the complexes have a prostaglandin content of 0.01–50% by weight, preferably 0.1–10% by weight and particularly preferably 0.2–1% by weight.

Surprisingly, the rate of degradation of the prostaglandins in the complexes according to the invention is reduced to such an extent that, on storage at a temperature of about 30° C. over a period of more than one year, the drop in content is significantly less than 10%. On the basis of the present results of investigations on prostaglandins of the E series, the complexes according to the invention are stable for more than 2 years and exhibit a drop in content of active compound of less than 8%.

The complexes can be processed, by themselves or with the addition of suitable auxiliaries, to solid or semi-solid and also injectable medicament forms as well as to sprays or inhalants. Examples of suitable auxiliaries are starch, cellulose, sugars, mannitol, polyvinylpyrrolidone, talc, stearic acid and salts thereof, long-chain aliphatics, such as, for example, hydrogenated castor oil or cottonseed oil, waxes, fats and liquid, semi-solid and solid hydrocarbons, as well as polyethylene glycols, emulsifiers and other pharmaceutical auxiliaries.

Solid medicament forms, such as tablets, capsules and powders, can be prepared by means of direct tabletting or direct filling of the pure complexes or also with addition of further auxiliaries, as well as via the intermediate stage of a granulation and/or mixing operation. Auxiliaries which are preferably used for the preparation of tablets, capsules or powders are starch, cellulose, sugars, mannitol, polyvinylpyrrolidone, talc and stearic acid and salts thereof, and also long-chain aliphatics, particularly preferably dried starch, microcrystalline cellulose or cellulose powder and hydrogenated castor oil or cottonseed oil.

The complexes can also be processed to ointments, creams, gels, pastes, suppositories and other semi-solid medicament forms by dispersion in fats, waxes, solid, semi-solid or liquid hydrocarbons, polyethylene glycols, emulsifiers and the like. It is also possible to prepare sprays, inhalants, tampons or plasters based on these adsorbates.

Such products are stable for years at room temperature.

The medicaments according to the invention contain prostaglandins, adsorbed onto crosspovidone, pre-pasted starch or dextrans, in amounts of 0.001 to 10% by weight, preferably 0.01 to 1% by weight and particularly preferably 0.03 to 0.3% by weight, if appropriate together with the above-mentioned auxiliaries. A typical medicament formulation has the following composition (data in % by weight):

| | |
|---|---|
| Active compound (prostaglandin PGE): | 0.01–1 |
| Dextran, Crosspovidone, pre-pasted starch (referred to as adsorber later on) | 1–99.9 |
| Water: | 0.1–5 | or, if axuliaries are used:

|   | preferably | particularly preferably |
|---|---|---|
| a. Tablets: | | |
| Active compound | 0.001–10 | 0.01–3 | 0.003–1 |
| Adsorber | 1–99 | 5–90 | 10–60 |
| Cellulose | 0–50 | 1–30 | 5–20 |
| Maize starch | 0–50 | 1–30 | 5–20 |
| Hydrogenated castor oil | 0–5 | 0.1–1 | 0.2–0.5 |
| Residual water | 0.5–15 | 1–10 | 2–6 |
| b. Capsules: | | |
| Active compound | 0.01–10 | 0.01–3 | 0.03–1 |
| Adsorber | 1–99 | 5–90 | 10–60 |
| Residual water | 0.1–15 | 0.5–10 | 1–5 |
| Gelatin | 10–90 | 20–80 | 30–50 |
| c. Powders | | |
| Active compound | 0.001–10 | 0.01–3 | 0.03–1 |
| Adsorber | 1–99 | 5–90 | 10–60 |
| Microcrystalline cellulose | 0–50 | 1–30 | 5–20 |
| Pre-pasted starch | 0–50 | 1–30 | 5–20 |
| residual water | 0,1–15 | 0,5–10 | 1–5 |

Tablets or capsules containing prostaglandins and crosspovidone, pre-pasted starch or dextrans are used as the preferred formulation in the context of the present invention. Tablets which are pressed in the abovementioned compositions and, if required, provided with a shell are preferred here. The capsule shell preferably consists of gelatin or another polymer soluble in the gastrointestinal tract. The tablets, as well as the capsules, can additionally be provided with a further shell or lacquer for improving stability or handling or to achieve a desirable retarding effect. A lacquer which is resistant to gastric juice can be applied so that controlled use of the agent in the duodenal and the area of the small intestine can be effected. Cellulose derivatives (preferably: methyl-, ethyl-, hydroxypropyl-, hydroxypropylmethyl-, cellulose acetate phthalate or hydroxypropylmethylcellulose phthalate), polymeric acrylates or copolymers thereof with other substances, usually with the addition of plasticisers, can be used as film-forming agents. If required, the shells can be provided with coloured or colouring substances. Other auxiliaries or flavour substances or active compounds can be present either in the shells or in the tablets or capsules or in both.

In the tablet or capsule formulations, the above-mentioned ranges of active compound/crosspovidone or pre-pasted starch or dextran ratio, water content and active compound content are also preferred ranges, also with any desired combination of the given ranges with one another.

According to the invention, it is also possible to mix several prostaglandin active compounds with one another in the desired rtio and to convert the mixture to the desired formulation, in which case the percentages by weight relate to the total content of active compound and cannot be included additively. the same is valid for the absorbers.

According to the invention, prostaglandins of the E series are also particularly preferred for the tablet or capsule formulation, and of these, the 16-methyl-1-11α, 16RS-Trihydroxyprost-13E-en-9one of the formula (I) already described above is particularly preferred.

The following prostaglandins are also preferred in the context of the present invention:

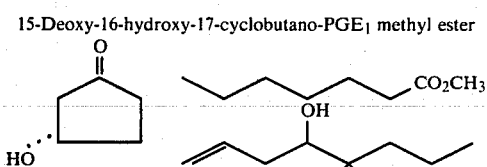

15-Deoxy-16-hydroxy-17-cyclobutano-PGE$_1$ methyl ester    II

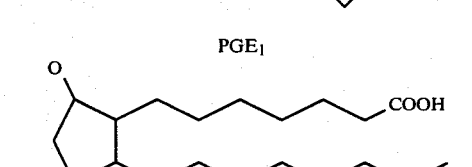

PGE$_1$    III

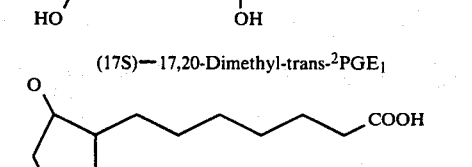

(17S)—17,20-Dimethyl-trans-$^2$PGE$_1$    IV

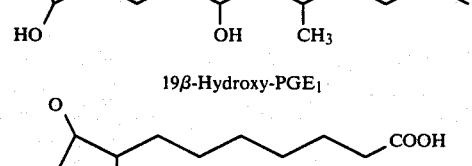

19β-Hydroxy-PGE$_1$    V

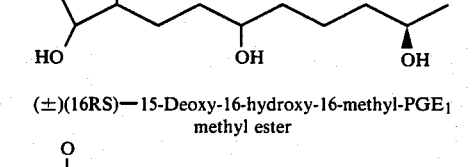

(±)(16RS)—15-Deoxy-16-hydroxy-16-methyl-PGE$_1$ methyl ester    VI

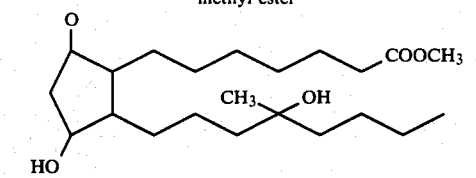

16,16-Dimethyl-trans-Δ$^2$-PGE$_1$ methyl ester    VII

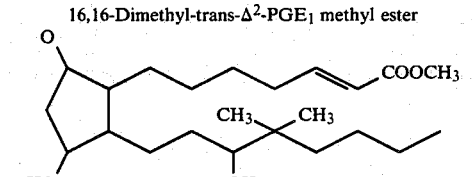

2-Decarboxy-2-hydroxy-methyl-PGE$_1$    VIII

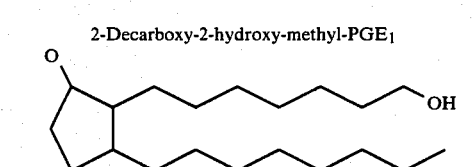

(+)-11α,16α,β-Dihydroxy-1,9-dioxo-1-(hydroxymethyl)-16-methyl-13-transprosiene    IX -continued
4,5,6-Trinor-3,7-inter-m-phenylene-3-oxa-PGE₁

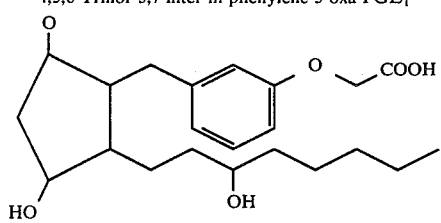

PGE₂

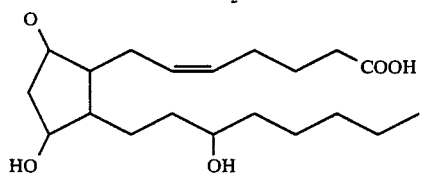

(15R)—15-Methyl-PGE₂

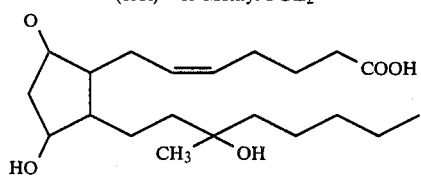

16,16-Dimethyl-PGE₂

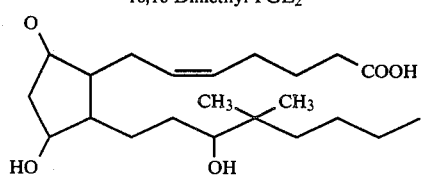

16-Methyl-20-methoxy-PGE₂    XIV

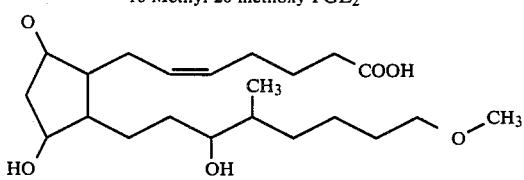

(±)(16RS)—15-Deoxy-16-hydroxy-16-methyl-PGE₂    XV
methyl ester

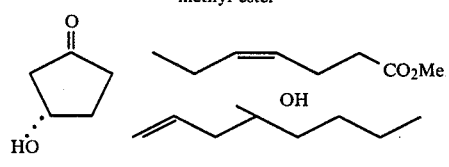

(+)-4,5-Didehydro-16-phenoxy-ω-tetranor-PGE₁    XVI
methyl ester

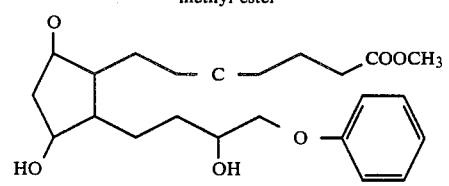

N—Methane-sulphonyl-10-phenoxy-ω-    XVII
tetranor-PGE₂-amide

-continued

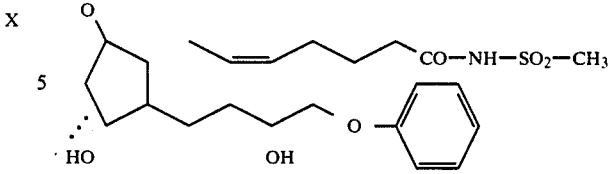

9-Deoxo-9-methylene-16,16-dimethyl-PGE₂    XVIII

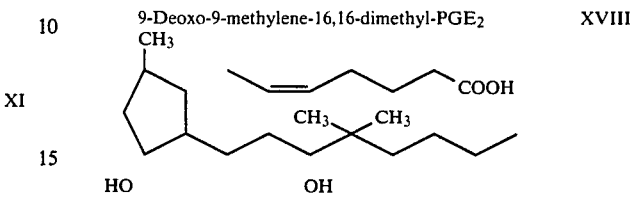

The prostaglandins according to the invention which are bonded to crosspovidone, pre-pasted starch or dextrans the complexes prepared by the process according to the invention and the formulations and tablets and capsules are used as medicaments. The complexes according to the invention are preferably used for combating gastrointestinal ulcers, hypertension, bronchial asthma and thromboses and for inducing labour or abortion in humans and animals, i.e. mammals. They are preferably used for combating gastrointestinal ulcers, and preferably in the form of tablets, capsules and suppositories. An especially preferred use in the combination: active compound/Dextrans in injectable or formulations.

In the following examples adsorber does mean Crosspovidone, pre-pasted starch or dextrans. In case absorber is used it does mean that the examples have been performed with all three absorbers: Crosspovidence, pre-pasted starch and dextrans in the amounts and formulations given.

The examples which follow are intended to illustrate the present invention in more detail:

EXAMPLE 1

5.0 g of active compound of the formula I are dissolved in 150 ml of ethanol and 450 ml of water.

995.0 g of adsorber are suspended in 5 liters of water, the suspension is stirred intensively with the above solution and the mixture is poured into dishes and dried by means of freeze-drying. The lyophilisate is passed through a sieve of 0.5 mm mesh width and is further processed as follows:

(A) Tablets Containing 0.1 mg of Active Compound of the Formula I 200 g of lyophilisate, 300 g of crosspovidone, 200 g of cellulose powder, 95 g of dried maize starch and 5 g of hydrogenated castor oil are mixed and the mixture is pressed to tablets weighing 80.0 mg.

(B) Capsules Containing 0.1 mg of Active Compound of the Formula I 200 g of lyophilisate and 300 g of crosspovidone are mixed and this mixture is filled into size 4 hard gelatin capsules containing 50.0 mg.

(c) Powder Containing 0.3 mg of Active Compound of the Formula I 5,000 g of maize starch, 3,700 g of microcrystalline cellulose and 300 g of pre-pasted maize starch are mixed and the mixture is granulated with water. The granules are dried and passed through a sieve of 0.8 mm mesh width.

600 g of lyophilisate, 400 g of crosspovidone and 9,000 g of the above granules are mixed, the mixture is filled into sachets containing 1.0 g and these are closed. The sachets can be made of paper, aluminium foil or an inert polymer film suitable for pharmaceutical purposes. The sachets can be stuck, welded or closed by any other method, if necessary with exclusion of air and if necessary under an inert gas, depending on the material. In carrying out the examples, paper sachets which were stuck were used.

(D) Cream—100 g Containing 15 mg of Active Compound of the Formula I

An oil and an emulsifier phase consisting of 120 g of 2-octyl-dodecanol, 100 g of cetyl stearyl alcohol, 20 g of synthetic spermaceti, 15 g of sorbitan monostearate and 10 g of polyoxyethylene-20 sorbitan monostearate are warmed to 60° C. and melted. 705 g of water are then added and the mixture is lasted intensively until a homogeneous cream is formed.

After cooling, 30 g of lyophilisate are added and the mixture is stirred intensively.

The finished cream is filled into tubes containing 100 g.

(E) Ointment—100 g Containing 15 mg of Active Compound of the Formula I 30 g of lyophilisate are triturated with 150 g of white petroleum jelly until a homogeneous mass has formed. This is then stirred intensively with 820 g of white petroleum jelly to give an ointment, and the ointment is filled, for example, into tubes containing 100 g.

(F) Suppositories Containing 0.5 mg of Active Compound of the Formula I 950 g of adeps solidus, as the suppository base, are warmed to about 42° C, 50 g of lyophilisate are homogenously suspended therein and the mixture is poured into suppository moulds containing 2 g. On cooling, the mass solidifies to the finished suppositories.

Table 1 which follows shows tablet formulations for the active compound of the formula I, 16-methyl-1-11α,16RS-trihydroxyprost-13E-en-9-one, as an adsorbate on crosspovidone, pre-pasted starch or dextran, with diverse auxiliaries in the ranges preferred according to the invention. All the weight data are in mg.

TABLE 1a

Examples of tablet formulations

| No. | Formula I | Cross-povidone | Cellulose powder | Microcrystal-line cellulose | Maize starch | Mannitol | Cross-povidone | Hydrogenated castor oil | Magnesium stearate |
|---|---|---|---|---|---|---|---|---|---|
| 1 | 0.01 | 1.0 | 50 | — | 25 | — | 3.79 | 0.2 | — |
| 2 | 0.01 | 2.0 | — | 50 | 25 | — | 2.79 | 0.2 | — |
| 3 | 0.01 | 5.0 | 50 | — | 20 | — | 3.79 | — | 0.2 |
| 4 | 0.01 | 2.0 | 50 | — | 27.69 | 40 | — | 0.3 | — |
| 5 | 0.01 | 5.0 | — | 50 | 24.69 | 40 | — | — | 0.3 |
| 6 | 0.03 | 3.0 | 50 | — | 23.77 | — | 3.0 | 0.2 | — |
| 7 | 0.03 | 6.0 | — | 50 | 8.77 | 15 | — | — | 0.2 |
| 8 | 0.03 | 15.0 | 30 | — | 14.77 | 20 | — | 0.2 | — |
| 9 | 0.03 | 6.0 | — | 50 | 28.67 | 30 | 5.0 | 0.3 | — |
| 10 | 0.03 | 15.0 | 70 | — | 34.67 | — | — | — | 0.3 |
| 11 | 0.05 | 5.0 | 50 | — | 21.75 | — | 3.0 | 0.2 | — |
| 12 | 0.05 | 10.0 | — | 30 | 19.75 | 20 | — | — | 0.2 |
| 13 | 0.05 | 25.0 | 25 | — | 9.75 | 20 | — | 0.2 | — |
| 14 | 0.05 | 10.0 | 70 | — | 11.65 | 20 | — | 0.3 | — |
| 15 | 0.05 | 25.0 | — | 50 | 39.65 | — | 5.0 | — | 0.3 |
| 16 | 0.1 | 10.0 | 30 | — | 19.7 | 20 | — | 0.2 | — |
| 17 | 0.1 | 20.0 | 30 | — | 26.7 | — | 3.0 | — | 0.2 |
| 18 | 0.1 | 50.0 | — | 20 | 9.7 | — | 3.0 | — | 0.2 |
| 19 | 0.1 | 20.0 | 50 | — | 19.6 | 30 | — | 0.3 | — |
| 20 | 0.1 | 50.0 | — | 40 | 24.6 | — | 5.0 | — | 0.3 |
| 21 | 0.3 | 30.0 | 30 | — | 19.5 | — | — | 0.2 | — |
| 22 | 0.3 | 60.0 | — | 10 | 9.5 | — | — | — | 0.2 |
| 23 | 0.3 | 150.0 | — | 20 | 19.3 | 10 | — | — | 0.4 |
| 24 | 0.3 | 60.0 | 40 | — | 9.4 | 10 | — | 0.3 | — |
| 25 | 0.3 | 150.0 | 80 | — | 59.2 | — | 10 | — | 0.5 |
| 26 | 0.6 | 60.0 | 10 | — | 9.2 | — | — | 0.2 | — |
| 27 | 0.6 | 120.0 | 30 | — | 22.0 | 20 | 7.0 | — | 0.4 |
| 28 | 0.6 | 60.0 | 40 | — | 19.1 | — | — | 0.3 | — |
| 29 | 1.0 | 100.0 | — | 70 | 28.5 | — | — | — | 0.5 |

TABLE 1

Examples of tablet formulations

| No. | Formula I | Pre-pasted maize starch | Dextran | Cellulose powder | Microcrystal-line cellulose | Maize starch | Mannitol | Cross-povidone | Hydrogen-ated castor oil | Magnesium stearate |
|---|---|---|---|---|---|---|---|---|---|---|
| 1 | 0.01 | 1.0 | | 50 | — | 28.79 | — | — | 0.2 | — |
| 2 | 0.01 | 2.0 | | — | 50 | 27.79 | — | — | — | 0.2 |
| 3 | 0.01 | 5.0 | | — | 50 | 19.79 | — | 5.0 | — | 0.2 |
| 4 | 0.01 | 2.0 | | 60 | — | 27.69 | 30 | — | 0.3 | — |
| 5 | 0.01 | 5.0 | | — | 60 | 24.69 | 30 | — | — | 0.3 |
| 6 | 0.03 | 3.0 | | 50 | — | 26.77 | — | — | 0.2 | — |
| 7 | 0.03 | 6.0 | | 50 | — | 18.77 | — | 5.0 | 0.2 | — |
| 8 | 0.03 | 15.0 | | 30 | — | 4.77 | — | 30 | — | 0.2 |
| 9 | 0.03 | 6.0 | | — | 60 | 23.67 | 30 | — | — | 0.3 |
| 10 | 0.03 | 15.0 | | — | 60 | 14.67 | — | 30 | — | 0.3 |
| 11 | 0.05 | 5.0 | | 50 | — | 19.75 | — | 5 | 0.2 | — |

TABLE 1-continued

Examples of tablet formulations

| No. | Formula I | Pre-pasted maize starch | Dextran | Cellulose powder | Microcrystal-line cellulose | Maize starch | Mannitol | Cross-povidone | Hydrogenated castor oil | Magnesium stearate |
|---|---|---|---|---|---|---|---|---|---|---|
| 12 | 0.05 | 10.0 | | 50 | — | 9.75 | — | 10 | 0.2 | — |
| 13 | 0.05 | 25.0 | | — | 20 | 24.65 | — | 50 | — | 0.3 |
| 14 | 0.05 | 10.0 | | 50 | — | 29.65 | 20 | 10 | 0.3 | — |
| 15 | 0.05 | 5.0 | | — | 50 | 24.65 | 30 | 10 | — | 0.3 |
| 16 | 0.1 | 10 | | — | 50 | 9.7 | — | 10 | 0.2 | — |
| 17 | 0.1 | 20 | | 40 | — | 19.6 | — | 40 | — | 0.3 |
| 18 | 0.1 | 50 | | 60 | — | 39.5 | — | 150 | — | 0.4 |
| 19 | 0.1 | 10 | | 60 | — | 39.6 | — | 10 | 0.3 | — |
| 20 | 0.1 | | 20.0 | — | 100 | 39.5 | — | 40 | — | 0.4 |
| 21 | 0.3 | | 30.0 | — | 20 | 9.4 | — | 60 | 0.3 | — |
| 22 | 0.3 | | 60.0 | 10 | — | 9.3 | — | 120 | 0.4 | — |
| 23 | 0.3 | | 150.0 | — | 100 | 48.7 | — | 300 | — | 1.0 |
| 24 | 0.3 | | 30.0 | 100 | — | 9.3 | — | 60 | 0.4 | — |
| 25 | 0.3 | | 60.0 | 60 | — | 29.2 | — | 150 | — | 0.5 |
| 26 | 0.6 | | 60.0 | — | 10 | 9.0 | — | 120 | — | 0.4 |
| 27 | 0.6 | | 120.0 | — | 120 | 58.4 | — | 300 | 1.0 | — |
| 28 | 0.6 | | 60.0 | 60 | — | 28.9 | — | 150 | 0.5 | — |
| 29 | 1.0 | | 100.0 | 150 | — | 48.8 | — | 300 | 1.0 | — |

Table 2 which follows shows capsule formulations for the active compound 16-methyl-1,11α-16RS-trihydroxyprost-13E-en-9one, formula I, as an complex on crossprovidone, where relevant with the addition of other auxiliaries, in mg.

TABLE 2

Examples of capsule formulations of active substance of the formula I

| No. | Formula I | Cross-povidone | Cellulose | Maize starch | Lactose | Magnesium stearate |
|---|---|---|---|---|---|---|
| 1 | 0.01 | 1.0 | 15 | 3.49 | 20 | 0.5 |
| 2 | 0.01 | 2.0 | 10 | 7.99 | 20 | — |
| 3 | 0.01 | 5.0 | 30 | 4.49 | 10 | 0.5 |
| 4 | 0.01 | 35.0 | — | 4.99 | — | — |
| 5 | 0.01 | 25.0 | 10 | 4.99 | — | — |
| 6 | 0.03 | 3.0 | 15 | 6.47 | 15 | 0.5 |
| 7 | 0.03 | 6.0 | 15 | 8.47 | 10 | 0.5 |
| 8 | 0.03 | 15.0 | 15 | 9.97 | — | — |
| 9 | 0.03 | 36.0 | — | 3.97 | — | — |
| 10 | 0.03 | 45.0 | 15 | 9.97 | — | — |
| 11 | 0.05 | 5.0 | 15 | 9.47 | 10 | 0.5 |
| 12 | 0.05 | 10.0 | 15 | 14.95 | — | — |
| 13 | 0.05 | 25.0 | 10 | 4.95 | — | — |
| 14 | 0.05 | 30.0 | 5 | 4.95 | — | — |
| 15 | 0.05 | 45.0 | 15 | 9.95 | — | — |
| 16 | 0.1 | 10.0 | 15 | 14.9 | — | — |
| 17 | 0.1 | 20.0 | 10 | 9.9 | — | — |
| 18 | 0.1 | 50.0 | 10 | 9.9 | — | — |
| 19 | 0.1 | 30.0 | 5 | 4.9 | — | — |
| 20 | 0.1 | 39.9 | — | — | — | — |
| 21 | 0.3 | 30.0 | 5 | 4.7 | — | — |
| 22 | 0.3 | 60.0 | 5 | 4.7 | — | — |
| 23 | 0.3 | 150.0 | — | — | — | — |
| 24 | 0.3 | 39.7 | — | — | — | — |
| 25 | 0.3 | 60.0 | 15 | 9.2 | 15 | 0.5 |

Tables 3 to 19 which follow show tablet formulations for various active compounds. All the data are in mg.

The following compounds were used as active compounds in the individual tablets:

| Table | Name | Formula |
|---|---|---|
| 3 | 15-Deoxy-16-hydroxy-17-cyclobutano-PGE$_1$ methyl ester | II |
| 4 | PGE$_1$ | III |
| 5 | (17S)—17,20-Dimethyl-trans-$\Delta^2$ PGE$_1$ | IV |
| 6 | 19β-Hydroxy-PGE$_1$ | V |
| 7 | (±) (16RS)—15-Deoxy-16-hydroxy-16-methyl-PGE$_1$ methyl ester | VI |
| 8 | 16,16-Dimethyl-trans-$\Delta^2$-PGE$_1$ methyl ester | VII |
| 9 | 2-Decarboxy-2-hydroxy-methyl-PGE$_1$ | VIII |
| 10 | (+)-11α,16α,β-Dihydroxy-1,9-dioxo-1-(hydroxymethyl)-16-methy-13-transprosiene | IX |
| 11 | 4,5,6-Trinor-3,7-inter-m-phenylene-3-oxa-PGE$_1$ | X |
| 12 | PGE$_2$ | XI |
| 13 | (15R)—15-methyl-PGE$_2$ | XII |
| 14 | 16,16-Dimethyl-PGE$_2$ | XIII |
| 15 | 16-Methyl-20-methoxy-PGE$_2$ | XIV |
| 16 | (±) (16RS)15-Deoxy-16-hydroxy-16-methyl-PGE$_2$ methyl ester | XV |
| 17 | (+)-4,5-Didehydro-16-phenoxy-ω-tetranor-PGE$_1$ methyl ester | XVI |
| 18 | N—methane-sulfonyl-10-phenoxy-ω-tetranor-PGE$_2$-amide | XVII |
| 19 | 9-Deoxo-9-methylene-16,16-dimethyl-PGE$_2$ | XVIII |

TABLE 3

Examples of tablet formulations

| No. | Formula II | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 4

Examples of tablet formulations

| No. | Formula III | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 5

Examples of tablet formulations

| No. | Formula IV | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 6

Examples of tablet formulations

| No. | Formula V | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 7

Examples of tablet formulations

| No. | Formula VI | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 8

Examples of tablet formulations

| No. | Formula VII | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 9

Examples of tablet formulations

| No. | Formula VIII | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 10

Examples of tablet formulations

| No. | Formula IX | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |

TABLE 10-continued

| | | | Examples of tablet formulations | | | | | | |
|---|---|---|---|---|---|---|---|---|---|
| No. | Formula IX | Cross-povidone | Cellulose powder | Microcrystalline cellulose | Maize starch | Mannitol | Polyvinyl-pyrrolidone | Hydrogenated castor oil | Magnesium stearate |
| 3 | 0.1 | 20.0 | 30 | — | 26 7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 11

| | | | Examples of tablet formulations | | | | | | |
|---|---|---|---|---|---|---|---|---|---|
| No. | Formula X | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 12

| | | | Examples of tablet formulations | | | | | | |
|---|---|---|---|---|---|---|---|---|---|
| No. | Formula XI | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 13

| | | | Examples of tablet formulations | | | | | | |
|---|---|---|---|---|---|---|---|---|---|
| No. | Formula XII | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 14

| | | | Examples of tablet formulations | | | | | | |
|---|---|---|---|---|---|---|---|---|---|
| No. | Formula XII | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 15

| | | | Examples of tablet formulations | | | | | | |
|---|---|---|---|---|---|---|---|---|---|
| No. | Formula XIV | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 16

| | | | Examples of tablet formulations | | | | | | |
|---|---|---|---|---|---|---|---|---|---|
| No. | Formula XV | Cross-povidone | Cellulose powder | Microcrystalline cellulose | Maize starch | Mannitol | Polyvinyl-pyrrolidone | Hydrogenated castor oil | Magnesium stearate |
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |

TABLE 16-continued

Examples of tablet formulations

| No. | Formula XV | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 5 | 1.0 | 200.0 | — | 70 | 28.5 | — | — | — | 0.5 |

TABLE 17

Examples of tablet formulations

| No. | Formula XVI | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 18

Examples of tablet formulations

| No. | Formula XVII | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 19

Examples of tablet formulations

| No. | Formula XVIII | Cross-povidone | Cellulose powder | Microcrystalline cellulose | Maize starch | Mannitol | Polyvinyl-pyrrolidone | Hydrogenated castor oil | Magnesium stearate |
|---|---|---|---|---|---|---|---|---|---|
| 1 | 0.01 | 2.0 | 50 | — | 24.79 | — | 3.0 | 0.2 | — |
| 2 | 0.03 | 6.0 | — | 50 | 8.77 | 15 | — | — | 0.2 |
| 3 | 0.1 | 20.0 | 30 | — | 26.7 | — | 3.0 | 0.2 | — |
| 4 | 0.3 | 60.0 | 40 | — | 1.4 | 10 | — | 0.3 | — |
| 5 | 1.0 | 200.0 | — | 70 | 28.5 | — | — | — | 0.5 |

TABLE 20

Examples of capsule formulations

| No. | Formula II | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 21

Examples of capsule formulations

| No. | Formula II | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 22

Examples of capsule formulations

| No. | Formula II | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 23

Examples of capsule formulations

| No. | Formula V | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 24

Examples of capsule formulations

| No. | Formula VI | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 25
Examples of capsule formulations

| No. | Formula VII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 26
Examples of capsule formulations

| No. | Formula VIII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 27
Examples of capsule formulations

| No. | Formula IX | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 28
Examples of capsule formulations

| No. | Formula X | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 29
Examples of capsule formulations

| No. | Formula XI | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 30
Examples of capsule formulations

| No. | Formula XII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 31
Examples of capsule formulations

| No. | Formula XIII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 32
Examples of capsule formulations

| No. | Formula XIV | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 33
Examples of capsule formulations

| No. | Formula XV | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 34
Examples of capsule formulations

| No. | Formula XVI | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 35
Examples of capsule formulations

| No. | Formula XVII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

TABLE 36
Examples of capsule formulations

| No. | Formula XVIII | Crosspovidone | Cellulose powder | Maize starch |
|---|---|---|---|---|
| 1 | 0.01 | 20.0 | 15 | 4.99 |
| 2 | 0.03 | 36.0 | — | 3.97 |
| 3 | 0.05 | 30.0 | — | 9.95 |
| 4 | 0.1 | 20.0 | 10 | 9.9 |
| 5 | 0.3 | 60.0 | — | 9.7 |

We claim:

1. A complex of 16-methyl-1-11α,16RS-Trihydroxyprost-13E-en-9-one of the formula (I)

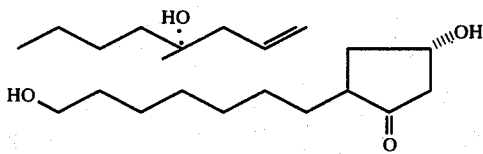

with crosspovidone, having a prostaglandin content of 0.01–50% by weight.

2. A complex of claim 1 having a prostaglandin content of 0.1 to 10% by weight.

3. A complex of claim 1 having a prostaglandin content of 0.2 to 1.0% by weight.

4. A pharmaceutical composition useful in the treatment of hypertension, bronchial asthma, gastrointestinal ulcers and thrombosis and for inducing labor and abortion in mammals containing as an active ingredient, a pharmaceutically effective amount of a complex according to claim 1 together with an inert pharmaceutical carrier.

5. A composition of claim 4 in the form of a sterile or physiologically isotonic aqueous solution.

6. A medicament in dosage unit form useful in the treatment of hypertension, bronchial asthma, gastrointestinal ulcers and thrombosis and for inducing labor and abortion in mammals comprising a pharmaceutically effective amount of complex according to claim 1 and an inert pharmaceutical carrier.

7. A medicament of claim 6 in the form of tablets, pills, dragees, capsules, ampouls, suppositories or creams.

8. A method of combatting gastrointestinal ulcers in warm-blooded animals which comprises administering to the animals an effective amount of an active complex according to claim 1 either alone or in admixture with a diluent or in the form of a medicament.

9. A method according to claim 8 in which the active complex is administered orally or parenterally.

10. A medicament containing 16-methyl-1,11,16-RS-Trihydroxyprost-13E-en-9one of the formula

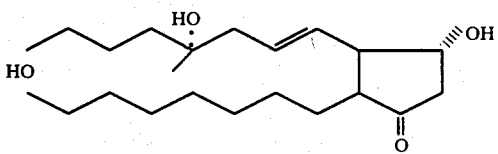

bonded to crossprovidone in an amount of 0.001 to 10 by weight.

* * * * *